(12) United States Patent
Hong et al.

(10) Patent No.: US 11,896,715 B2
(45) Date of Patent: Feb. 13, 2024

(54) IN VIVO BULKING AGENT, INJECTION COMPRISING SAME, AND PREPARATION METHOD THEREFOR

(71) Applicant: KOREA UNIVERSITY RESEARCH AND BUSINESS FOUNDATION, Seoul (KR)

(72) Inventors: Kwang Dae Hong, Gyeonggi-do (KR); Jihun Seo, Seoul (KR); Joon Bum Lee, Chungcheongbuk-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 37 days.

(21) Appl. No.: 17/621,587

(22) PCT Filed: Jun. 11, 2020

(86) PCT No.: PCT/KR2020/007557
§ 371 (c)(1),
(2) Date: Dec. 21, 2021

(87) PCT Pub. No.: WO2020/256340
PCT Pub. Date: Dec. 24, 2020

(65) Prior Publication Data
US 2022/0354790 A1    Nov. 10, 2022

(30) Foreign Application Priority Data

Jun. 21, 2019  (KR) .................. 10-2019-0073898
Jun. 25, 2019  (KR) .................. 10-2019-0075727

(51) Int. Cl.
| A61K 47/36 | (2006.01) |
| A61K 47/42 | (2017.01) |
| A61K 9/16  | (2006.01) |
| A61K 9/00  | (2006.01) |
| A61K 9/50  | (2006.01) |

(52) U.S. Cl.
CPC .......... *A61K 9/1641* (2013.01); *A61K 9/0019* (2013.01); *A61K 9/5026* (2013.01); *A61K 47/36* (2013.01); *A61K 47/42* (2013.01)

(58) Field of Classification Search
None
See application file for complete search history.

(56) References Cited

U.S. PATENT DOCUMENTS

2014/0065221 A1* 3/2014 Eloy .................. A61K 8/25
514/777

FOREIGN PATENT DOCUMENTS

| CN | 101541313 A | 9/2009 |
| CN | 102702798 A | 10/2012 |
| CN | 106421897 A | 2/2017 |
| EP | 0730847 A1 | 9/1996 |
| JP | 2009045221 | 3/2009 |
| JP | 2012503524 | 2/2012 |
| JP | 2014510590 | 5/2014 |
| KR | 101528741 | 6/2015 |
| TW | 200734423 A | 9/2007 |

OTHER PUBLICATIONS

Herz et al., "Efficacy of Endoscopic Subureteral Polydimethylsiloxane Injection for Treatment of Vesicoureteral Reflux in Children: A North American Clinical Report," The Journal of Urology, 2001, vol. 166. (Year: 2001).*
Kang et al., "Inhibition of Foreign Body Reactions on the Surfaces of Artificial Implant Materials Using Zwitterionic Polymers," 2017, Polymer Science and Technology, vol. 28, No. 5. (Year: 2017).*
Radley et al., Transurethral implantation of silicone polymer for stress incontinence: evaluation of a porcine model and mechanism of action in vivo, 2000, BJU International, 85, 646-650, DOI: 10.1046/j.1464-410x.2000.00515.x (Year: 2000).*
Garapaty et al., "Non-covalent phosphorylcholine coating reduces protein adsorption and phagocytic uptake of microparticles," Chem Comm., 2015, vol. 51. (Year: 2015).*
Garapaty et al., "Non-covalent phosphorylcholine coating reduces protein adsorption and phagocytic uptake of microparticles," Chem Comm., 2015, vol. 51.
Herz et al., "Efficacy of Endoscopic Subureteral Polydimethylsiloxane Injection for Treatment of Vesicoureteral Reflux in Children: A North American Clinical Report," The Journal of Urology, 2001, vol. 166.
Kang et al., "Inhibition of Foreign Body Reactions on the Surfaces of Artificial Implant Materials Using Zwitterionic Polymers," 2017, Polymer Science and Technology, vol. 28, No. 5.
WIPO, International Search Report for PCT/KR2020/007557, dated Nov. 25, 2020.

* cited by examiner

*Primary Examiner* — Mark V Stevens
*Assistant Examiner* — Katherine Siller
(74) *Attorney, Agent, or Firm* — Hodgson Russ LLP (57) ABSTRACT

The present invention relates to an in-vivo bulking agent which can be used as a medicinal agent for prevention or treatment of at least one disease selected from the group consisting of urinary incontinence, fecal incontinence, and gastroesophageal reflux or as a filler for use in a plastic surgery procedure, and to a preparation method therefor. The in-vivo bulking agent can exhibit a bulking effect when injected into the body and particularly, is highly biocompatible because a first composition in which silicone particles are coated with a zwitterionic polymer having a surfactant property is introduced into a second composition, whereby the bulking agent can inhibit inflammatory reactions in vivo.

14 Claims, 8 Drawing Sheets

Prepare first composition in which zwitterionic polymer is surrounded on surface of silicone particles ~ S100

Disperse first composition in second composition having viscosity of 100 to 1500 cps at room temperature ~ S200

IN VIVO BULKING AGENT, INJECTION COMPRISING SAME, AND PREPARATION METHOD THEREFOR

TECHNICAL FIELD

The present disclosure relates to an in-vivo bulking agent and a preparation method therefor, and more particularly, to an in-vivo bulking agent which can exhibit a bulking effect when injected into the body, and can be used as a medicinal agent for prevention or treatment of at least one disease selected from the group consisting of urinary incontinence, fecal incontinence, and gastroesophageal reflux or as a filler for use in a plastic surgery procedure, and to a preparation method therefor.

BACKGROUND ART

Urinary incontinence is defined by the International Continence Society as a social or sanitary problem caused by abnormal urination in which urine leaks regardless of one's will.

As for the incidence of urinary incontinence in Korea, it is reported that about 30% of the middle-aged female population complains of urinary incontinence, and the incidence in the elderly is much higher, indicating a high frequency of 40% or more when being housed in a care facility. Although urinary incontinence is not life-threatening like tumors or other wasting diseases, the discomfort and shame caused by urinary incontinence, and consequent restrictions on social activities can lead to gradual isolation and psychological disorders.

Urinary incontinence is one of the most difficult incurable diseases to be solved by modern medicine. While more than 50% of cancer patients in Korea can be cured, there is still no reliable treatment for fecal incontinence. Urinary incontinence is not easy to treat because it occurs as a result of various factors, including anal sphincter and nervous system abnormalities that affect the anatomical physiology of the anorectum. Although drugs, behavioral therapy, and sphincteroplasty are being combined and treated appropriately, the effect is insignificant, and scientific evidence is insufficient.

Currently, for the treatment of urinary incontinence patients, sacral nerve stimulation, etc. is performed in extremely exceptional cases in Korea, but the therapeutic effect decreases with time, and the treatment mechanism is not clear, either. In addition, patients with a lot of radiofrequency thermal energy therapy and artificial sphincter activity, or patients who require a lot of treatment for urinary incontinence eventually have to live their whole life with a stoma on the abdominal wall as a terminal treatment, and related complications cannot be avoided.

Fecal incontinence is a chronic disease that greatly affects the quality of life of patients and restricts social activities, and is difficult to treat. Currently, there is no non-invasive treatment other than surgical treatment for patients who are ineffective in drug treatment in Korea. Therefore, the method of treating fecal incontinence by administering a bulking agent between the anal sphincter or submucosa to create a passive barrier can be easily implemented for use in an office setting, and can be attempted as an intermediate treatment for patients who do not respond to drugs. So far, only NSAHA Dx (tradename Solesta) using Sweden Q-Med's dextranomer core has proven its effectiveness through a large-scale randomized controlled study, and is the only FDA-approved bulking agent for fecal incontinence.

As for these injections, silicone, silicone-based agent, pyrolytic carbon-coated ceramic beads (Durasphere), autologous fat, glutaraldehyde cross-linked collagen (GAX collagen), polytetrafluoroethylene (Polytef), etc. are injected and used in the weakened anal sphincter, but they are expensive and additional injection due to movement of the injected material to other parts and reoperation are required. In addition, the material injected into the anal sphincter causes an inflammatory response. To date, no agent has been developed that shows durability and safety for a long period of time due to excellent biocompatibility and price satisfaction.

Related Patent: Japanese Patent Laid-Open No. 2009-45221

DISCLOSURE OF THE INVENTION

Technical Goals

The present disclosure is directed to addressing an issue associated with the related art, and to providing an in-vivo bulking agent which can exhibit a bulking effect when injected into the body and can reduce inflammatory responses in vivo and a preparation method therefor.

Technical Solutions

In order to achieve the above purpose, in one embodiment, the present disclosure provides an in-vivo bulking agent, including:

a first composition including silicone particles and a zwitterionic polymer surrounding a surface of silicone particles; and a second composition having a viscosity of 100 to 1500 cps at room temperature, in which the zwitterionic polymer of the first composition has a surfactant property.

In addition, in one embodiment, the present disclosure provides an injection including an in-vivo bulking agent.

In addition, in one embodiment, the present disclosure provides a method for preventing or treating a sphincter-related disease, in which the method includes injecting an in-vivo bulking agent into a subject.

In addition, in one embodiment, the present disclosure provides a method for preparing an in-vivo bulking agent, in which the method includes: mixing silicone particles and a zwitterionic polymer to prepare a first composition in which the zwitterionic polymer is surrounded on a surface of silicone particles; and dispersing the first composition in a second composition having a viscosity of 100 to 1500 cps at room temperature.

Effects

The in-vivo bulking agent according to one embodiment of the present disclosure can exhibit a bulking effect when injected into the body and is highly biocompatible because a first composition in which silicone particles are coated with a zwitterionic polymer having a surfactant property is introduced into a second composition, whereby the bulking agent can inhibit inflammatory responses in vivo.

Moreover, the in-vivo bulking agent according to one embodiment of the present disclosure can be applied to various uses requiring bulking in the body, including fecal incontinence, urinary incontinence, gastroesophageal reflux, vesicoureteral reflux, and fillers (prosthesis) used in cosmetic surgical procedures.

BEST MODE FOR CARRYING OUT THE INVENTION

The present disclosure may be modified in various forms, and specific embodiments thereof will be illustrated in the drawings and described in detail in the detailed description. However, this is not intended to limit the present disclosure to specific embodiments, and it should be understood that all modifications, equivalents and substitutes included in the spirit and technical scope of the present disclosure are included. In describing the present disclosure, when it is determined that a detailed description of a related known technology may obscure the gist of the present disclosure, the detailed description thereof will be omitted.

The terms used in the following description are used to merely describe specific embodiments, but are not intended to limit the present disclosure. The terms of a singular form may include plural forms, unless the context clearly indicates otherwise.

The terms such as "include" and "have" used herein are intended to indicate that features, numbers, steps, operations, elements, components, or combinations thereof used in the following description exist and it should be thus understood that the possibility of existence or addition of one or more different features, numbers, steps, operations, elements, components, or combinations thereof is not excluded.

The present disclosure relates to an in-vivo bulking agent which may exhibit a bulking effect when injected into the body and a preparation method therefor.

In particular, the in-vivo bulking agent according to the present disclosure may exhibit a bulking effect when injected into the body and is highly biocompatible because a first composition in which silicone particles are coated with a zwitterionic polymer having a surfactant property is introduced into a second composition, whereby the bulking agent may inhibit inflammatory responses in vivo.

Hereinafter, the present disclosure will be described in detail.

In one embodiment, the present disclosure provides an in-vivo bulking agent, including:

a first composition including silicone particles and a zwitterionic polymer surrounding a surface of silicone particles; and a second composition having a viscosity of 100 to 1500 cps at room temperature, in which the zwitterionic polymer of the first composition has a surfactant property.

The in-vivo bulking agent may be used for prevention or treatment of sphincter-related diseases, or may be used for cosmetic procedures. The sphincter-related disease refers to any disease occurring in relation to the sphincter, and may be a urinary incontinence disease, fecal incontinence, gastroesophageal reflux or vesicoureteral reflux. When used for the cosmetic procedure, the agent is used as a filler for the cosmetic procedure.

In the conventional in-vivo bulking agent, additional injection and reoperation are required as the material injected into the body moves to other organs along the lymph or blood vessels, and the material injected into the body causes an inflammatory response.

Accordingly, the present disclosure is directed to addressing an issue associated with the related art, and to providing an in-vivo bulking agent which may exhibit a bulking effect when injected into the body and is highly biocompatible because a first composition in which silicone particles are coated with a zwitterionic polymer having a surfactant property is introduced into a second composition, whereby the bulking agent may inhibit inflammatory responses in vivo.

Prior to the description, among the terms used in the present disclosure, the term "in-vivo bulking agent" is a bulking agent capable of maintaining a predetermined volume in the body of a subject, and may refer to a kind of filler or implant.

In addition, among the terms used in the present disclosure, the term "target", "subject" or "patient" may be the subject of treatment, observation, or experiment, and may be a vertebrate. In certain embodiments, the vertebrate is a mammal. The mammals include, but are not limited to, farm animals (such as cows), sport animals, pets (such as guinea pigs, cats, dogs, rabbits, and horses), primates, mice and rats. In certain embodiments, the vertebrate may be a human, and in embodiments including administering an in-vivo bulking agent, the subject may be a patient typically in need of such administration.

Moreover, among the terms used in the present disclosure, the term "zwitterionic polymer" may refer to a polymer having two or more functional groups having opposite charges.

At least one functional group has a positive electrical charge and the other one has a negative electrical charge, so that a net charge becomes zero. The zwitterionic polymer according to the present disclosure may have opposite charges and may have a surfactant property. More specifically, the zwitterionic polymer may be a copolymer including a monomer having a hydrophilic group and a monomer having a hydrophobic group.

First, the first composition of the present disclosure will be described in detail below.

In one embodiment of the present disclosure, the first composition may include silicone particles and a zwitterionic polymer surrounding a surface of silicone particles.

The first composition is preferably injected into the body. To this end, it is best to have a spherical shape, which is the easiest form for injection, considering the efficiency of injection into the body. The average particle diameter of the spherical microparticles may be 50 to 500 μm, or 100 to 200 μm in consideration of the ease of injection into the body and introduction of a physiologically active material. When the average diameter of the first composition is less than 50 μm, movement (loss) in the body may occur due to a biological phenomenon, and when the average diameter of the first composition exceeds 500 μm, the diameter of the first composition may be too large to be dispersed in the second composition to be described later. When used as an injection, it may be clogged with the inner diameter of the injection needle, making it difficult to use as an injection agent.

The silicone particles are organic silicon compounds, and may be polydimethylsiloxane (PDMS), and preferably may be silicone particles modified to be hydrophilic.

In addition, the zwitterionic polymer may have a surfactant property having hydrophilicity and hydrophobicity, and may be a random copolymer including a first monomer having a zwitterion ion and a second monomer containing an acrylic acid ester. More specifically, the first monomer may be one or more selected from the group consisting of methacryloyloxyethyl phosphorylcholine (MPC), carboxybetaine methacrylate (CBMA), and sulfobetaine methacrylate (SBMA), and the second monomer may be one or more selected from the group consisting of butyl methacrylate (BMA), 3-[tris(trimethylsiloxy)silyl]propyl methacrylate (TRIS) and dodecyl methacrylate (DMA). As an example, the zwitterionic polymer may be poly(MPC-ran-BMA (PMB) which is a binary random copolymer obtained by copolymerizing methacryloyloxyethyl phosphorylcholine (MPC), a cell membrane mimicking zwitterion, with butyl methacrylate (BMA), a hydrophobic monomer. The mole fractions of MPC and BMA may be 30 to 70% and 70 to 30%, respectively. For example, the MPC and BMA may be synthesized by adding a mole fraction of 1:1. However, the present disclosure is not limited thereto.

The methacryloyloxyethyl phosphorylcholine (MPC) has a so-called zwitterion structure having both a cation and an anion in one molecule, and this chemical group has high polarity, is electrically neutral, and is a hydrogen bond acceptor and non-hydrogen bond donor. It is known as an ideal molecular structure to secure biocompatibility from an early stage. For this reason, MPC has been used for the purpose of imparting biocompatibility to the surfaces of various biomaterials used in the biological environment, such as artificial blood vessels, artificial hearts, and artificial joints, and its stability is also verified and is a representative synthetic material approved by the FDA.

In one embodiment of the present disclosure, the PMB polymer coated on the surface of the silicone particles is composed of BMA containing a butyl group capable of interacting with hydrophobic silicone particles, and the strong hydrophobic interaction of BMA with the silicone particles enables the adsorption of hydrophilic MPC components to the silicone particle surface stably in water.

When the molar ratio of MPC in the PMB polymer is less than the above range or when the molar ratio of BMA exceeds the above range, it may be difficult to ensure biocompatibility in an in-vivo bulking agent. When the molar ratio of MPC exceeds the above range or when the molar ratio of BMA is less than the above range, the amount of BMA compared to MPC is small, and thus it may be difficult to stably adsorb the hydrophilic MPC components to the silicone particle surface in water.

In other words, the in-vivo bulking agent of the present disclosure is highly biocompatible because a zwitterionic polymer having a surfactant property is coated on silicone particles, whereby the bulking agent may inhibit inflammatory responses in vivo.

Next, the second composition according to one embodiment of the present disclosure will be described in detail below.

The second composition is a viscous material having a predetermined viscosity, and has a viscosity of 100 to 1500 cps at room temperature.

In particular, since the second composition has a predetermined viscosity, the addition to an in-vivo bulking agent may resolve a rapid sinking of the particles of the first composition. Accordingly, a certain amount of the first composition may be injected into the body.

The molecular weight of the second composition may be 500,000 to 3,000,000 Da, 700,000 to 2,000,000 Da, 800,000 to 1,500,000 Da, or 1,000,000 Da. Since the second composition has a relatively small molecular weight and a predetermined viscosity, it may resolve a rapid sinking of the particles included in the first composition.

In addition, the second composition may have a viscosity of 100 to 1500 cps at room temperature, may have a viscosity of 100 to 900 cps, and preferably may have a viscosity of 100 to 350 cps.

More specifically, when the viscosity of the second composition at room temperature is less than 100 cps, the viscosity is small, and thus it is not possible to resolve a rapid sinking of the particles included in the first composition. When the viscosity exceeds 1500 cps, the viscosity is very high, and thus, when injected into tissue, it may be difficult to inject due to high pressure.

In one embodiment of the present disclosure, the second composition may include a biocompatible viscous material, and the biocompatible viscous material may be hyaluronic acid (HA) or collagen, but is not limited thereto.

Preferably, the biocompatible viscous material may be hyaluronic acid.

In one embodiment of the present disclosure, the second composition may be added in an amount of 55% (v/v) to 65% (v/v) based on the total in-vivo bulking agent.

More specifically, when the second composition is included at less than 55% (v/v) with respect to the total in-vivo bulking agent, the suspension retention time of the in-vivo bulking agent is short, so that the particles of the first composition quickly sink, and thus it may be difficult to inject a certain amount into the tissue. In particular, when the second composition is injected into the tissue, an excessive amount may be injected at once or the composition spreads too quickly to the surrounding area.

In addition, with respect to the total in-vivo bulking agent, when the second composition exceeds 65% (v/v), the amount of the first composition, which has the main bulking effect, is relatively small, thereby making it difficult to achieve the expected effect of the invention.

In one aspect, the second composition of the in-vivo bulking agent may be added at an average of 60% (v/v) while being loaded in a syringe including an 18 to 26 G needle.

The injection may further include a diluent or excipient such as a filler, an extender, a binder, a wetting agent, a disintegrant, a surfactant, etc. commonly used for injections in the pharmaceutical field, in addition to the in-vivo bulking agent.

The in-vivo bulking agent according to one embodiment of the present disclosure satisfies the following Equation 1:

$$|V_2-V_1|\times 1/100 \leq 0.1 \quad \text{[Equation 1]}$$

in which, $V_1$ refers to a volume occupied by the in-vivo bulking agent when the in-vivo bulking agent is injected into a subject, and $V_2$ refers to a volume occupied by the in-vivo bulking agent in the body 4 weeks after injection of the in-vivo bulking agent into the subject.

Preferably, the in-vivo bulking agent according to an embodiment of the present disclosure may satisfy the following Equation 2:

$$|V_2-V_1|\times 1/100 \leq 0.05 \quad \text{[Equation 2]}$$

In other words, the in-vivo bulking agent according to one embodiment of the present disclosure may maintain its volume even after a predetermined period of time has elapsed after being injected into a subject, and may maintain 90% or more of the volume when first injected into the subject.

Moreover, the in-vivo bulking agent of the present disclosure may exhibit effects of suppressing protein adsorption in a subject and suppressing inflammation and the like.

Figure 1:
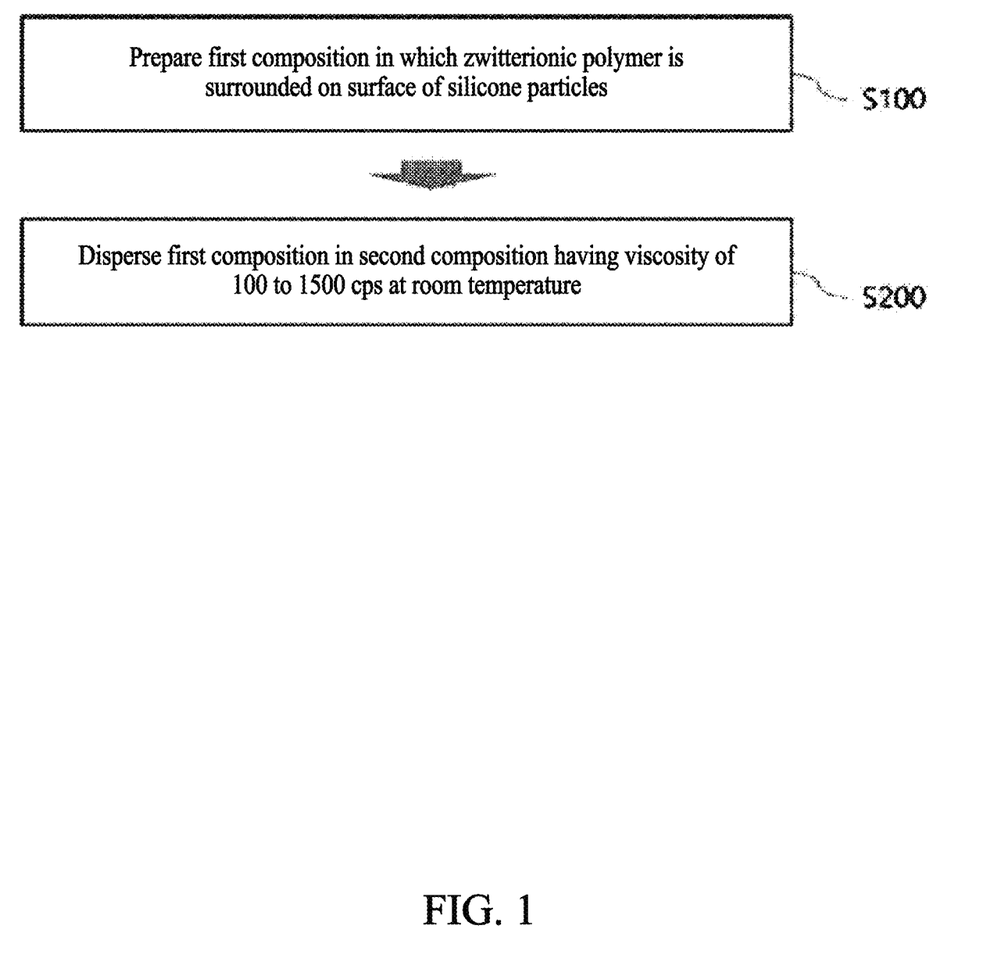
FIG. 1 is a flowchart of a method for preparing an in-vivo bulking agent according to the present disclosure.

According to one embodiment of the present disclosure, there is provided a method for preparing an in-vivo bulking agent, in which the method includes: mixing silicone particles and a zwitterionic polymer to prepare a first composition in which the zwitterionic polymer is surrounded on a surface of silicone particles (S100); and dispersing the first composition in a second composition having a viscosity of 100 to 1500 cps at room temperature (S200) (see FIG. 1).

First, the preparation of the first composition includes: preparing a mixed solution by adding silicone particles and a zwitterionic polymer to a solvent (S110); dispersing the silicone particles and the zwitterionic polymer in the solvent by ultrasonicating and stirring the mixed solution (S120); and centrifuging the dispersed mixed solution to obtain a powder (S130).

The solvent may be any material as long as it is a solvent capable of dispersing silicone particles and an amphoteric polymer. As the solvent, purified water, methyl alcohol, ethyl alcohol, isopropyl alcohol, dimethyl sulfoxide, etc. may be used, and for example, purified water may be used.

In addition, the silicone particle is an organic silicon compound, and may be polydimethylsiloxane (PDMS), and preferably may be a silicone particle modified to be hydrophilic.

In addition, the zwitterionic polymer may have a surfactant property having hydrophilicity and hydrophobicity, and may be a random copolymer including a first monomer having a zwitterion ion and a second monomer containing an acrylic acid ester. More specifically, the first monomer may be one or more selected from the group consisting of methacryloyloxyethyl phosphorylcholine (MPC), carboxybetaine methacrylate (CBMA), and sulfobetaine methacrylate (SBMA), and the second monomer may be one or more selected from the group consisting of butyl methacrylate (BMA), 3-[tris(trimethylsiloxy)silyl]propyl methacrylate (TRIS) and dodecyl methacrylate (DMA). As an example, the zwitterionic polymer may be poly(MPC-ran-BMA (PMB) which is a binary random copolymer obtained by copolymerizing methacryloyloxyethyl phosphorylcholine (MPC), a cell membrane mimicking zwitterion, with butyl methacrylate (BMA), a hydrophobic monomer. The mole fractions of MPC and BMA may be 30 to 70% and 70 to 30%, respectively. For example, the MPC and BMA may be synthesized by adding a mole fraction of 1:1. However, the present disclosure is not limited thereto.

The mixed solution may contain 0.1 to 5 parts by weight of the zwitterionic polymer based on 100 parts by weight of the silicone particles, and more specifically, 0.3 to 4 parts by weight of the zwitterionic polymer based on 100 parts by weight of the silicone particles, 0.5 to 3 parts by weight, 0.8 to 2 parts by weight, or 1 part by weight. When the amount of the zwitterionic polymer added as compared to the silicone particles added to the solvent is less than the above range, the amount of the zwitterionic polymer is too small to easily coat the silicone particles. When the amount of the zwitterionic polymer added as compared to the silicone particles added to the solvent exceeds the above range, the shape or particle size of the PDMS may be affected due to changes in the interfacial properties of a medium. Accordingly, the above range may be preferred. For example, 1.1 g of PDMS and 10 mg of PMB may be added to 10 mL of purified water and mixed.

In this case, a dispersant may be further added to the solvent. Specifically, the dispersant may be polyvinylpyrrolidone (PVP), cetyltrimethylammonium bromide (CTAB), or polyethylene glycol (PEG), and for example, the dispersant may be polyvinylpyrrolidone (PVP). The dispersant may be added in an amount of 10 to 35 parts by weight based on 100 parts by weight of the silicone particles. As an example, 250 mg of PVP may be added to the mixed solution.

In addition, by applying ultrasonic waves to the mixed solution, the silicone particles and the zwitterionic polymer may be dispersed in the solvent. For example, the mixed solution may be re-dispersed by generating ultrasonic waves with an ultrasonic generator to disperse the silicone particles for 5 minutes and then performing a vortex again for 5 minutes.

Next, a process of stirring the ultrasonically treated solution at a rotation speed of 500 to 2000 rpm or 1500 rpm at room temperature may be performed. As described above, when the mixed solution is stirred, a cured mixture may be obtained in which the silicone particles are dispersed. In addition, low-speed centrifugation may be performed. Specifically, the process of low-speed centrifugation-removal of supernatant-redispersion of purified water may be repeated several times.

In this case, particles having an average particle size of less than 50 μm may be removed. In addition, after high-speed centrifugation, the supernatant may be removed and the silicone particles in the aggregated form may be recovered through freeze-drying. Accordingly, the zwitterionic polymer-coated silicone particles (first composition) may be prepared.

The first composition may be spherical particles, and the average particle diameter of the spherical microparticles may be 50 to 500 μm, or 100 to 200 μm in consideration of the ease of injection into the body and introduction of a physiologically active material. When the average diameter of the first composition is less than 50 μm, movement (loss) in the body may occur due to a biological phenomenon, and when the average diameter of the first composition exceeds 500 μm, the diameter of the first composition may be too large to be dispersed in the second composition to be described later. When used as an injection, it may be clogged with the inner diameter of the injection needle, making it difficult to use as an injection agent.

Next, the method includes dispersing the first composition in a second composition having a viscosity of 100 to 1500 cps at room temperature (S200).

Specifically, since the second composition has a predetermined viscosity, the addition to an in-vivo bulking agent may resolve a rapid sinking of the particles of the first composition. Accordingly, a certain amount of the first composition may be injected into the body.

The molecular weight of the second composition may be 500,000 to 3,000,000 Da, 700,000 to 2,000,000 Da, 800,000 to 1,500,000 Da, or 1,000,000 Da. Since the second composition has a relatively small molecular weight and a predetermined viscosity, it may resolve a rapid sinking of the particles included in the first composition.

In addition, the second composition may have a viscosity of 100 to 1500 cps at room temperature, may have a viscosity of 100 to 900 cps, and preferably may have a viscosity of 100 to 350 cps.

More specifically, when the viscosity of the second composition at room temperature is less than 100 cps, the viscosity is small, and thus it is not possible to resolve a rapid sinking of the particles included in the first composition. When the viscosity exceeds 1500 cps, the viscosity is very high, and thus, when injected into tissue, it may be difficult to inject due to high pressure.

In one embodiment of the present disclosure, the second composition may include a biocompatible viscous material, and the biocompatible viscous material may be hyaluronic acid (HA) or collagen, but is not limited thereto.

Preferably, the biocompatible viscous material may be hyaluronic acid.

In one embodiment of the present disclosure, the second composition may be added in an amount of 55% (v/v) to 65% (v/v) based on the total in-vivo bulking agent.

More specifically, when the second composition is included at less than 55% (v/v) with respect to the total in-vivo bulking agent, the suspension retention time of the in-vivo bulking agent is short, so that the particles of the first composition quickly sink, and thus it may be difficult to inject a certain amount into the tissue. In particular, when the second composition is injected into the tissue, an excessive amount may be injected at once or the composition spreads too quickly to the surrounding area.

In addition, with respect to the total in-vivo bulking agent, when the second composition exceeds 65% (v/v), the amount of the first composition, which has the main bulking effect, is relatively small, thereby making it difficult to achieve the expected effect of the invention.

For example, the volume ratio to be added of the first composition and the second composition may be mixed in a ratio of about 4:6.

In addition, in one embodiment, the present disclosure provides a method for preventing or treating a sphincter-related disease, in which the method includes providing an injection containing the in-vivo bulking agent, and injecting the in-vivo bulking agent into a subject.

More specifically, the in-vivo bulking agent according to the present disclosure may be used for various uses that can exhibit a bulking effect when a medicament for preventing or treating at least one sphincter-related disease selected from the group consisting of fecal incontinence, rectal incontinence, gastroesophageal reflux, a urinary incontinence disease, and vesicoureteral reflux; and cosmetic plastic surgery fillers are injected into the body. The diseases listed above are only examples, but are not limited thereto.

Herein, the fecal incontinence disease mainly occurs in the population with old age, urinary incontinence, dementia, psychiatric disease, sphincter injury during childbirth, sphincter injury due to cancer removal surgery, chronic constipation, etc., and may be one or more selected from the group consisting of diabetes, Parkinson's disease, stroke, spinal cord injury, rectal prolapse, inflammatory bowel disease, radiation-related proctitis, and congenital anal anomaly, but is not limited thereto.

In the present disclosure, the term "subject" refers to a target in need of a method for preventing, controlling or treating a disease, and more specifically, a human or a mammal such as a non-human primate, a mouse, a rat, a dog, a cat, a horse and a cow.

The agent of the present disclosure is administered in a pharmaceutically effective amount. In the present disclosure, the term "pharmaceutically effective amount" refers to an amount that is sufficient to treat a disease at a reasonable benefit/risk ratio applicable to medical treatment. The effective dose level may be determined depending on factors including the type of a patient's disease, severity, drug activity, sensitivity to drugs, administration time, administration route, excretion rate, duration of treatment, and concomitant drugs, and other factors well known in the medical field. The agent according to the present disclosure may be administered as a single therapeutic agent or in combination with other therapeutic agents, and may be administered sequentially or simultaneously with conventional therapeutic agents. The agent may be administered in a single dosage or multiple dosages. Taking all of the above factors into consideration, it is important to administer an amount that may obtain the maximum effect with a minimum amount without side effects, and may be easily determined by those skilled in the art.

Specifically, the effective amount of the agent of the present disclosure may vary depending on the patient's age, sex, condition, weight, absorption of the active ingredient into the body, inactivation rate and excretion rate, disease type, and drugs used in combination, for example, 0.1 cc to 100 cc may be administered to an adult. However, the dosage may be increased or decreased depending on the route of administration, the severity of the disease, sex, weight, age, etc., and thus the dosage is not intended to limit the scope of the present disclosure in any way.

Hereinafter, the present disclosure will be described with reference to the following examples. However, the examples are for describing the present disclosure in detail, and the scope of the present disclosure is not limited to the following examples.

PREPARATION EXAMPLE

PMB (Poly(MPC-Ran-BMA) Polymer Synthesis

PMB, a random copolymer, was synthesized by copolymerizing MPC (2-methacryloyloxyethyl phosphorylcholine, KCI), a cell membrane mimicking zwitterion, with BMA (butyl methacrylate, TCI), a hydrophobic monomer.

In order to synthesize a PMB (Poly(MPC-ran-BMA) polymer, the reactants were synthesized at the following input ratios as follows (see Table 1).

TABLE 1

| | MPC (mmol) | BMA (mmol) | Ethanol | Toluene | AIBN (mmol) |
|---|---|---|---|---|---|
| Preparation example | 738.2 mg (2.5 mmol) | 355.5 mg (2.5 mmol) | 2500 μL | 2500 μL | 4.1 mg (0.025 mmol) |

738.2 mg of MPC, 355.5 mg of BMA, and 4.1 mg of AIBN were added to a mixed solvent of 2500 μL of ethyl alcohol and 2500 μL of toluene. After injecting high-purity argon gas into the mixture for 10 minutes, the reactor was sealed, and the mixture was magnetically stirred in a silicone oil bath at 60° C. for 24 hours. After stirring, the mixture was added dropwise to acetone in an excess of about 50 times the amount of the mixture and then filtered to obtain a white powder, which was then dispersed or dissolved in an aqueous solution and then recovered again through freeze-drying.

Preparation of Hyaluronic Acid (HA) Gel Formulation Injection

In order to prepare a hyaluronic acid gel formulation, the reactants were prepared by adding them as shown in Table 2 below (see Table 2).

TABLE 2

| | Purified water | 1 N NaOH aqueous solution | HA (1,000,000 Da) | BDDE |
|---|---|---|---|---|
| Preparation Example | 750 μl | 250 μl | 100 mg | 20 μl |

Specifically, 100 mg of hyaluronic acid (HA) (Alfa Aesar) having a number average molecular weight of 1,000,000 Da and 250 μl of 1 N NaOH aqueous solution were added to 750 μl of purified water. After stirring with a spatula to completely dissolve HA, 20 μl of BDDE was added as a crosslinking agent, followed by mixing and sealing, followed by reaction in a water bath at 50° C. for 3 hours to obtain a gel formulation mixture (HA 10% (w/v), crosslinking agent 2% (w/v)). After immersion in the purified water for 6 hours, the swollen gel was dialyzed against 800 mL of phosphate-buffered saline solution (PBS) at 35° C. for 3 days to recover the acid-neutralized gel.

EXAMPLES

Example 1. Preparation of In-Vivo Bulking Agent

PMB Polymer Coating on Silicone Particles

In order to coat the surface of the silicone microparticles with PMB, the reactants were prepared by adding them as shown in Table 3 below (see Table 3).

More specifically, 1.1 g of PDMS as a silicone material (a mixture of 1.0 g as an injection and 0.1 g as a curing agent) was defoamed for 30 minutes under vacuum at room temperature. To 1.1 g of the defoamed silicone, 10 mL of purified water, 250 mg of PVP as a dispersant, and 10 mg of PMB as a coating material to improve biocompatibility were added (PDMS 10% (w/v), PVP (polyvinylpyrrolidone) 2.5% (w/v), PMB 0.1% (w/v)).

TABLE 3

| | PDMS | Purified water | PVP | PMB |
|---|---|---|---|---|
| Examples | 1.1 g | 10 mL | 250 mg | 10 mg |

Figure 3:
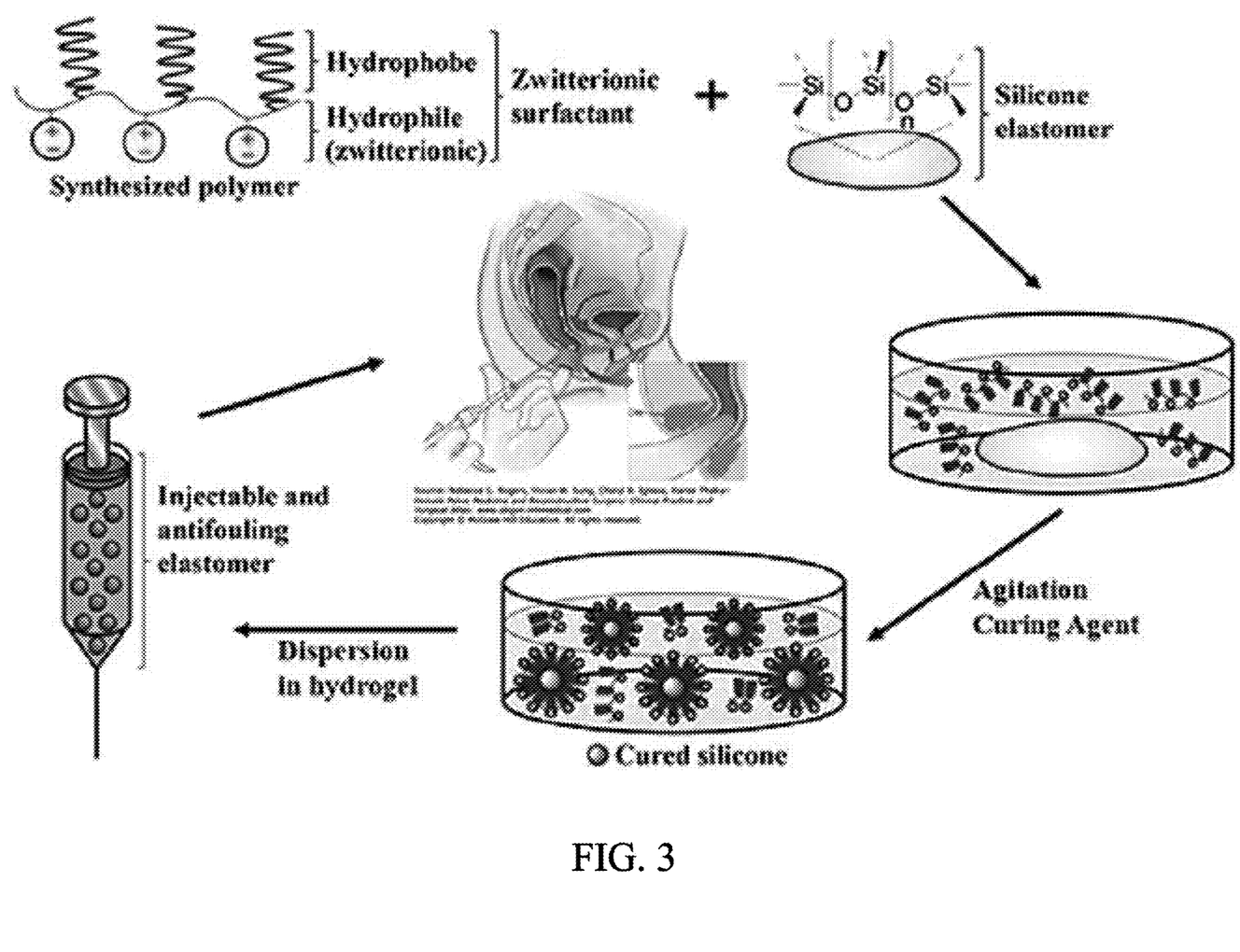
FIG. 3 is a view schematically showing the method for preparing an in-vivo bulking agent of Example 1.

The silicone particles were dispersed for 5 minutes by generating ultrasonic waves with an ultrasonic generator in the mixture, and then redispersed by a vortex for 5 minutes again. A magnetic stirring bar having a length of 75% or more of the diameter of the reactor was put and stirred at room temperature at a rotation speed of 1500 rpm for 4 days to obtain a cured mixture with silicone particles dispersed therein. The process of low-speed centrifugation-removal of supernatant-redispersion in purified water was repeated three times to remove particles having a size of less than 50 μm. After high-speed centrifugation, the supernatant was removed and the silicone particles in the aggregated form were recovered through freeze-drying (see FIG. 3).

In-Vivo Bulking Agent 400 mL of silicone microparticles were added to 600 mL of the prepared gel, compressed and stirred to loosen the agglomerated silicone microparticles, and at the same time crushed the gel to an appropriate size and dispersed the microparticles in the gel to prepare an in-vivo bulking agent for injection.

COMPARATIVE EXAMPLES

Comparative Example 1. No Surface Treatment on PDMS

Except that the PMB polymer was coated on the silicone particles, the same in-vivo bulking agent as in Example 1 was prepared.

Comparative Example 2. Preparation of Conventional Bulking Agent

As an FDA-approved bulking agent for pediatric urinary incontinence, an agent (Dexol, manufactured by Q-med) was prepared in which medical hyaluronic acid gel is a carrier in the detronomer core.

EXPERIMENTAL EXAMPLES

Experimental Example 1. Property Analysis of Surface Protein Adsorption

In order to indirectly identify the biocompatibility of the silicone particles coated with the PMB polymer prepared in the Examples in vitro, the adsorption strength of the fluorescently-labeled protein was evaluated. Protein adsorption properties of the silicone particles coated with the PMB polymer in Example 1 and the silicone particles of Comparative Example 1 were analyzed. In addition, the result is shown in FIG. 2.

FIG. 2(a) is a view showing the properties of the injection-type implants of the silicone microparticles prepared in the PMB surfactant polymer solution, and FIG. 2(b) is a view showing the results of analyzing the surface protein adsorption properties of the particles.

Figure 2:
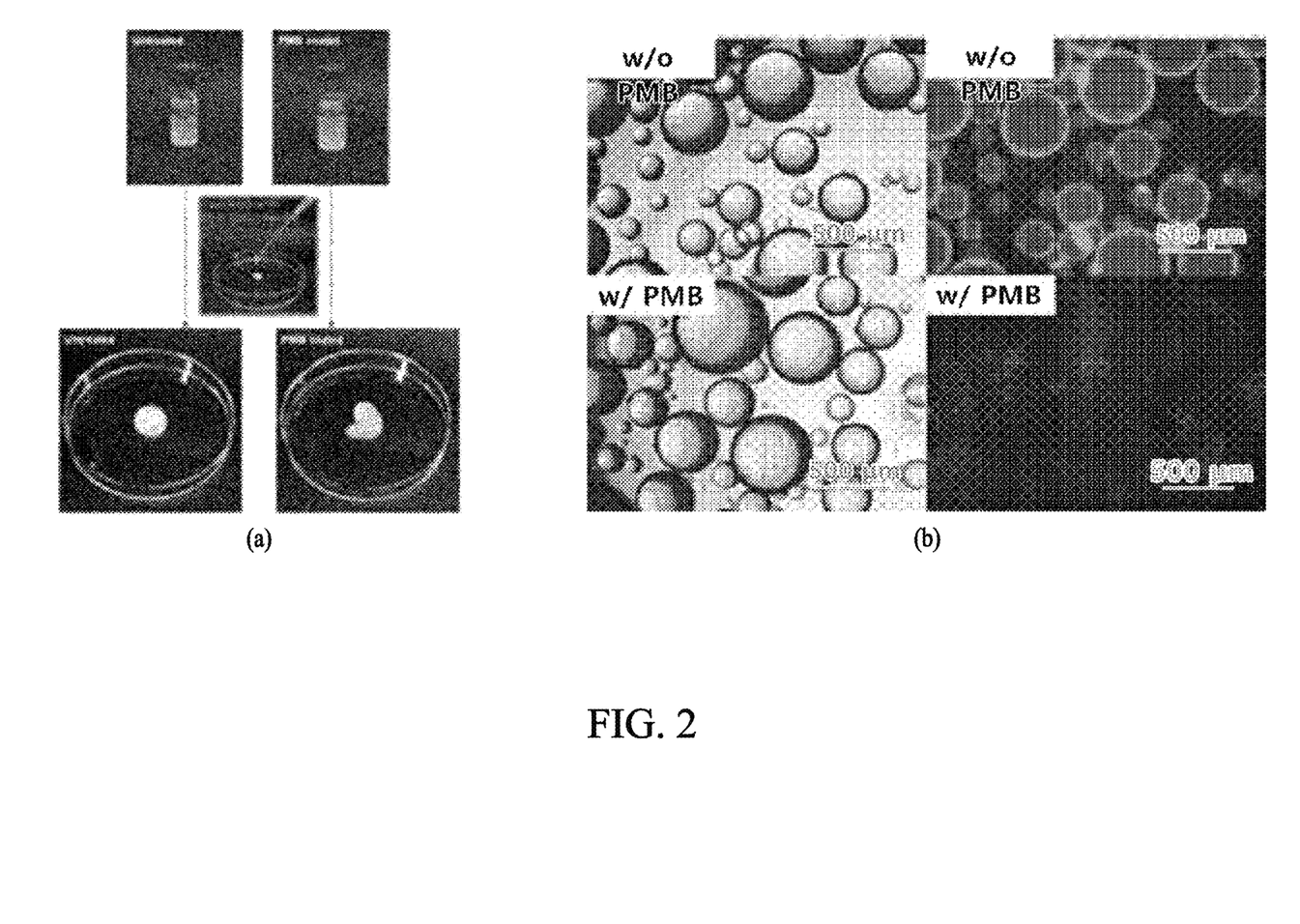
FIG. 2(a) is a view showing the properties of the injection-type implants of the silicone microparticles prepared in the PMB surfactant polymer solution.
FIG. 2(b) is a view showing the results of analyzing the surface protein adsorption properties of the particles.

Referring to FIG. 2, it was identified that almost no protein was adsorbed on the surface of silicone particles prepared as one-pot in PMB solution, compared that a large amount of protein was adsorbed in the case of silicone particles that were not coated with PMB.

Accordingly, it is determined that the silicone particles coated with the PMB polymer prepared in Example 1 have excellent biocompatibility.

Experimental Example 2. Measurement of Volume Change within Period (1 Week after Injection)

Laboratory Animals

In this experiment, 10 rats weighing 150-200 g and over 30 days old were used, and all experimental procedures including the selection and management of experimental animals and surgical treatment were carried out in accordance with the guidelines of the Animal Experimental Ethics Committee of Korea University Medical Center.

The feed and living conditions were kept constant, and the experiment was conducted after identifying that there were no abnormal signs after an acclimatization process for one week in an animal experimental laboratory.

Surgical Procedure of Laboratory Animals

First, Alfaxalone and Xylazine (Bayer Korea) were intramuscularly injected into each rat to induce general anesthesia. Then, the antibiotic Enfloxacin and the analgesic Ketoprofen were intramuscularly injected.

Setting up Experimental Groups

The experimental animals were divided into three groups and treated as follows.

Group 1: Group in which an in-vivo bulking agent of Example 1 was added (PMPC surface treatment on PDMS)

Group 2: Group in which an in-vivo bulking agent of Comparative Example 1 was added (no surface treatment on PDMS)

Group 3: Group in which an agent (Dexol) was added as an commercial bulking agent for pediatric urinary incontinence, in which medical hyaluronic acid gel is a carrier in the dextranomer core Injection 0.2 cc each of injection was injected into surgically treated experimental animals using an 18-gauge needle. Specifically, the needle was inserted into the sphincter in the direction of 7 o'clock in the anus of the rat to a depth of 5 mm. By injecting slowly and not withdrawing the needle for 30 seconds after the injection was completed, the injection was prevented from leaking along the needle tract.

Tissue Collection

Rats were euthanized in a $CO_2$ chamber one week after injection of the intumescent agent. Two rats in each of the three groups were tissue excised. Specifically, the tissues of the anal canal and systemic organs (liver, lung, kidney, lymph node) were excised.

State Analysis of Anal Tissue

In order to analyze the state of the anal tissue of rats one week after injection of the expandable agent, histological staining was performed by hematoxylin-eosin staining (H&E staining).

More specifically, the collected tissue was immersed in a 4% paraformaldehyde fixative and fixed at room temperature for 24 hours. After washing the fixed tissue with water, it was embedded in paraffin after decalcipification, clearing, and dehydration. After making tissue sections with a thickness of 4 μm, they were placed in a heating block at 60° C. for 45 minutes to deparaffinize. The process was sequentially subjected to xylene 3 times for 5 minutes each, 100% ethanol 3 times for 5 minutes each, 95% ethanol 2 times for 2 minutes each, 70% ethanol 2 times for 2 minutes each, and distilled water 2 times for 2 minutes each. After the hydration process, the tissue sections were sequentially subjected to 1% hematoxylin solution for 30 seconds, distilled water washing, 0.25% hydrogen chloride for 1 second, distilled water washing, and lithium carbonate color development to stain the nucleus. After staining the cytoplasm by treatment with eosin for 2 seconds, dehydration and clearing were performed, followed by mounting and observation under a microscope. In addition, it was treated with inflammatory factors TNF-α and Masson's trichrome staining.

Figure 4:
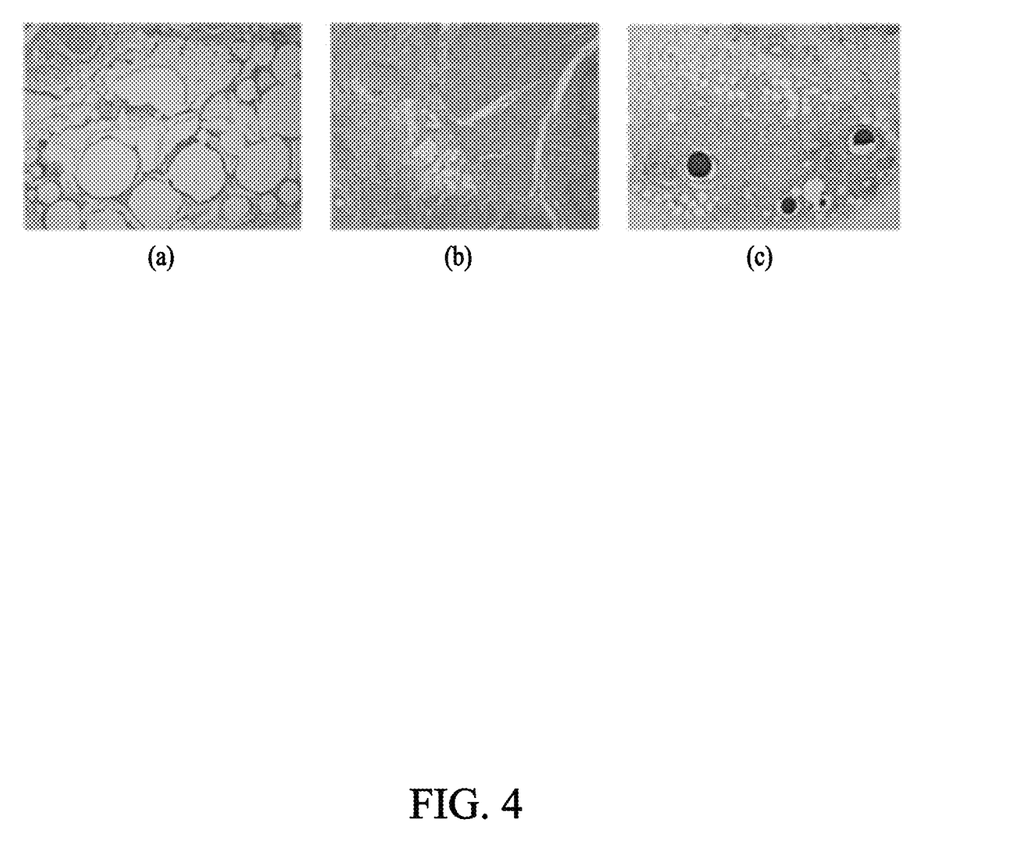
FIG. 4 is a view showing the results of 100-fold magnification with an optical microscope after H&E staining of anal tissue 1 week after injecting an injection into three groups in Experimental Example 1 ((a) Example 1, (b) Comparative Example 1, and (c) Comparative Example 2).

In addition, the result is shown in FIG. 4. FIG. 4 is a view showing the results of 100-fold magnification with an optical microscope after H&E staining of anal tissue 1 week after injecting an injection into three groups in Experimental Example 2 ((a) Example 1, (b) Comparative Example 1, and (c) Comparative Example 2 (Dexol)).

Referring to FIG. 4, it was identified in Example 1 that as an agent with PMPC surface treatment on PDMS, the particle size was preserved at 200 μm and the total volume did not change, so absorption in the tissue was weak. In addition, granulomatous inflammation was hardly observed (FIG. 4(a)).

It was identified in Comparative Example 1 that as an agent without surface treatment on PDMS, the particle size was very reduced, and only about 50% of the total volume remained compared to the group injected with one prepared in Example 1, so the injection was highly absorbed in the tissue. Peripheral inflammatory responses (multinucleated giant cells, lymphocytes, macrophage, etc.) were observed more than in FIG. 4(a) (FIG. 4(b)).

Dexol is a bulking agent used for pediatric urinary incontinence, and the total volume was reduced by about half compared to the group injected with one prepared in Example 1, so that absorption in the tissue occurred more than Example 1, but less than Comparative Example 1. In addition, it was identified that the peripheral inflammatory response was very severe (FIG. 4(c)).

In conclusion, it was identified that the agent of Example 1 had less peripheral inflammatory response, was hardly absorbed into the tissue, and also had little change in particle size.

State Analysis of Systemic Organ Tissue

For group 1, in which the in-vivo bulking agent of Example 1 was added, the state of the systematic organ tissue was analyzed.

When analyzing the state of anal tissue, histological staining of the systematic organs (liver, lung, kidney tissue, and lymph node) was performed using the same hematoxylin-eosin staining (H&E staining).

Figure 5:
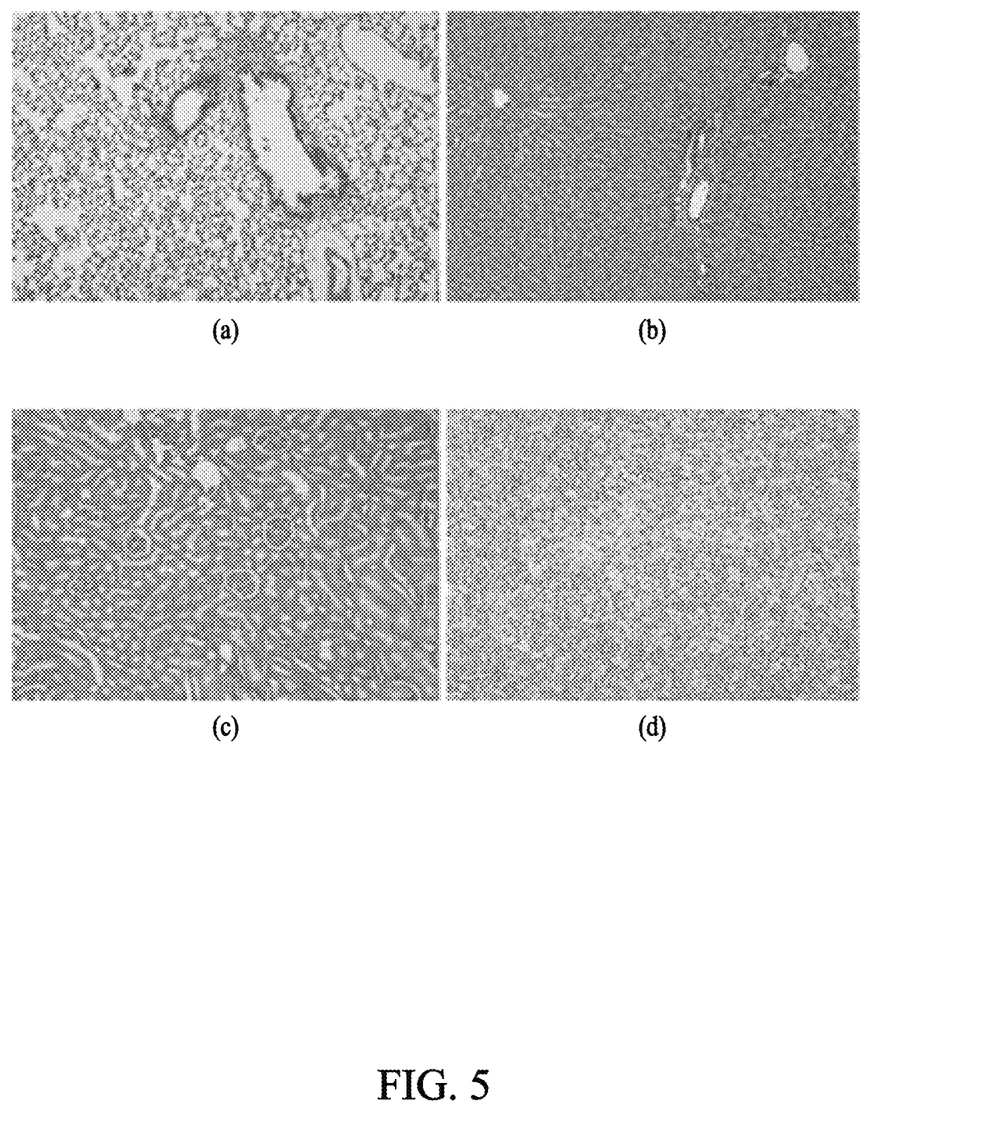
FIG. 5 is a view showing the results of 100-fold magnification with an optical microscope after H&E staining of the systemic tissue 1 week after injecting an injection of Example 1 into Group 1 in Experimental Example 1 ((a) lung 1, (b) liver, (c) kidney, and (d) lymph node).

In addition, the result is shown in FIG. 5.

FIG. 5 is a view showing the results of 100-fold magnification with an optical microscope after H&E staining of the systemic tissue 1 week after injecting an injection of Example 1 into Group 1 in Experimental Example 2 ((a) lung 1, (b) liver, (c) kidney, and (d) lymph node).

Referring to FIG. 5, no polymer compound was observed in the systemic organs, and no microscopic inflammatory response was observed, either.

It is determined that the agent of Example 1 does not move to other organs along lymph or blood vessels.

Experimental Example 3. Measurement of Volume Change within Period (4 Weeks after Injection)

State Analysis of Anal Tissue (H&E Stain)

After identifying that there were no abnormal signs after an acclimatization process for 4 weeks in an animal laboratory, the experiment was carried out, and the experiment was carried out in the same manner as in Experimental Example 1.

In order to analyze the state of the anal tissue of rats 4 weeks after injection of the expandable agent, the anal tissue of the experimental group was histologically stained by hematoxylin-eosin staining (H&E staining) in the same manner as in Experimental Example 2.

Figure 6:
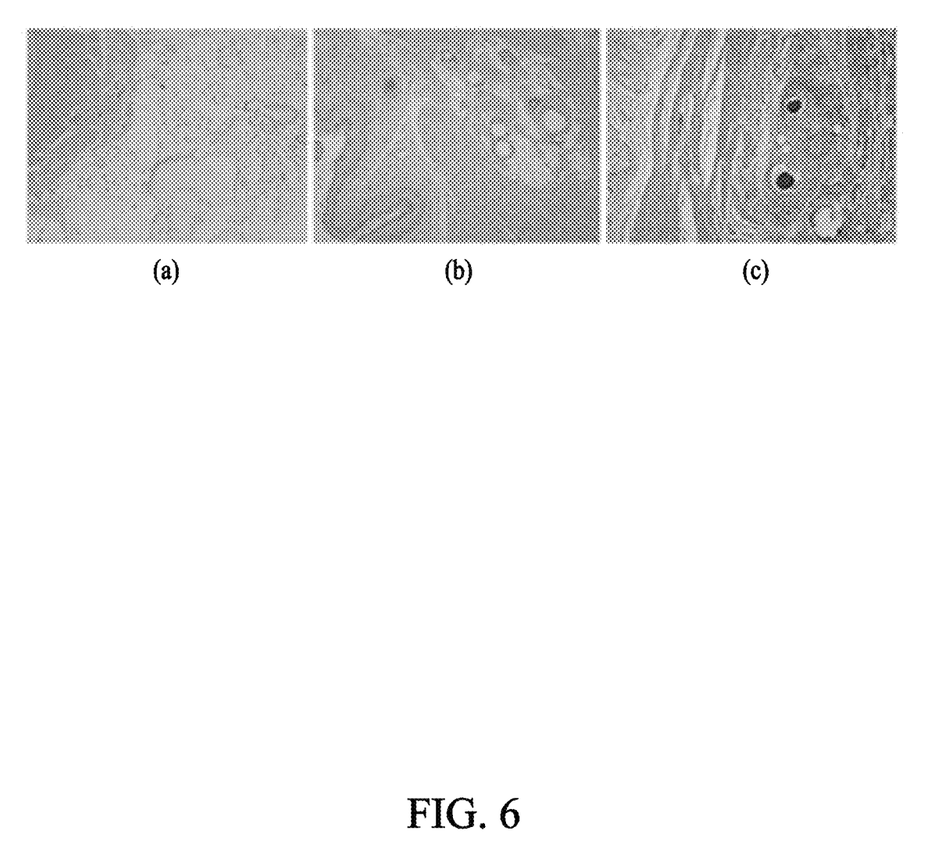
FIG. 6 is a view showing the results of each of 40-, 100-, and 100-fold magnification with an optical microscope after H&E staining of anal tissue 4 weeks after injecting an injection into three groups in Experimental Example 2 ((a) Example 1, (b) Comparative Example 1, and (c) Comparative Example 2).

In addition, the result is shown in FIG. 6. FIG. 6 is a view showing the results of each of 40-, 100-, and 100-fold magnification with an optical microscope after H&E staining of anal tissue 4 weeks after injecting an injection into three groups in Experimental Example 3 ((a) Example 1, (b) Comparative Example 1, and (c) Dexol).

Referring to FIG. 6(a), it was identified in Example 1 that as an agent with PMPC surface treatment on PDMS, the total volume change was not different from the result of Experimental Example 2 (week 1), identifying that absorption in the tissue was weak. In addition, granulomatous inflammation was hardly observed.

It was identified in Comparative Example 1 that as an agent without surface treatment on PDMS, the total volume also remained only about 10% compared to the group injected with one prepared in Example 1, identifying that the injection was highly absorbed into the tissue. In addition, peripheral inflammatory responses (multinucleated giant cells, lymphocytes, macrophages, etc.) were observed more than in FIG. 6(a) (FIG. 6(b)).

As for Dexol, compared to the group injected in Example 1, the total volume remained only about 10%, thus identifying a lot of absorption in the tissue. In addition, it was identified that the deposition of peripheral inflammatory cells and fibrosis were very severe (FIG. 6(c)).

In conclusion, the experimental group injected with the agent (Example 1) with PMPC surface treatment on PDMS did not change in volume compared to the first week, thus identifying that absorption into the tissue hardly occurred, and the inflammatory response was also less than that of the agent without surface treatment on PDMS (Comparative Example 1). Dexol used for pediatric urinary incontinence showed very severe inflammatory cells.

State Analysis of Anal Tissue (Mt Stain)

Figure 7:
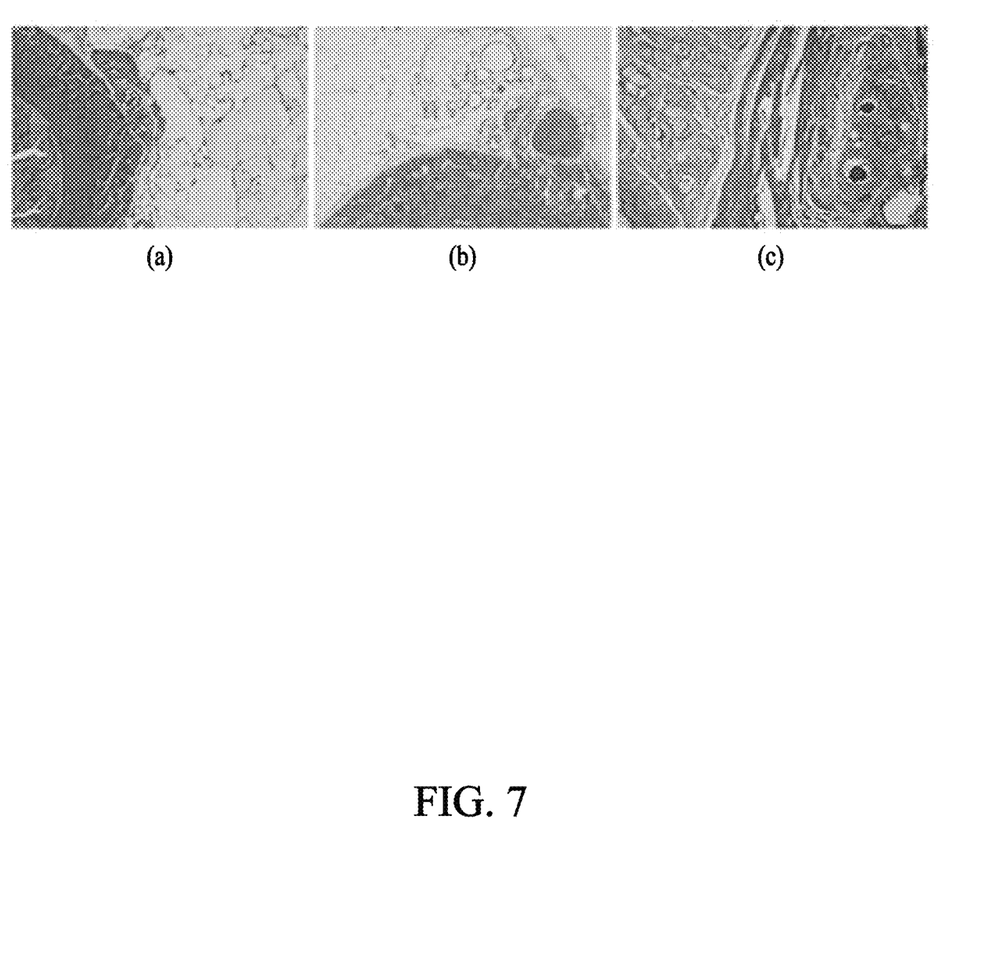
FIG. 7 is a view showing the results of 40-fold magnification with an optical microscope after MT staining of anal tissue 4 weeks after injecting an injection into three groups in Experimental Example 2 ((a) Example 1, (b) Comparative Example 1, and (c) Comparative Example 2).

The excised tissues of the experimental group were stained with Masson's trichrome (MT) staining method. Then, it was observed with an optical microscope. The results are shown in FIG. 7. FIG. 7 is a view showing the results of 40-fold magnification with an optical microscope after MT staining of anal tissue 4 weeks after injecting an injection into three groups in Experimental Example 3 ((a) Example 1, (b) Comparative Example 1, and (c) Dexol).

Referring to FIG. 7, although the difference in fibrosis is small in FIG. 7(a) and FIG. 7(b), it was identified that a thick fibrotic band was formed around the particles in FIG. 7(c).

State Analysis of Anal Tissue (TNF-α Immunostaining)

In order to analyze the cells expressing the inflammatory cytokines expressed in the experimental group, TNF-α staining was performed, and it was observed with an optical microscope. The results are shown in FIG. 8.

Figure 8:
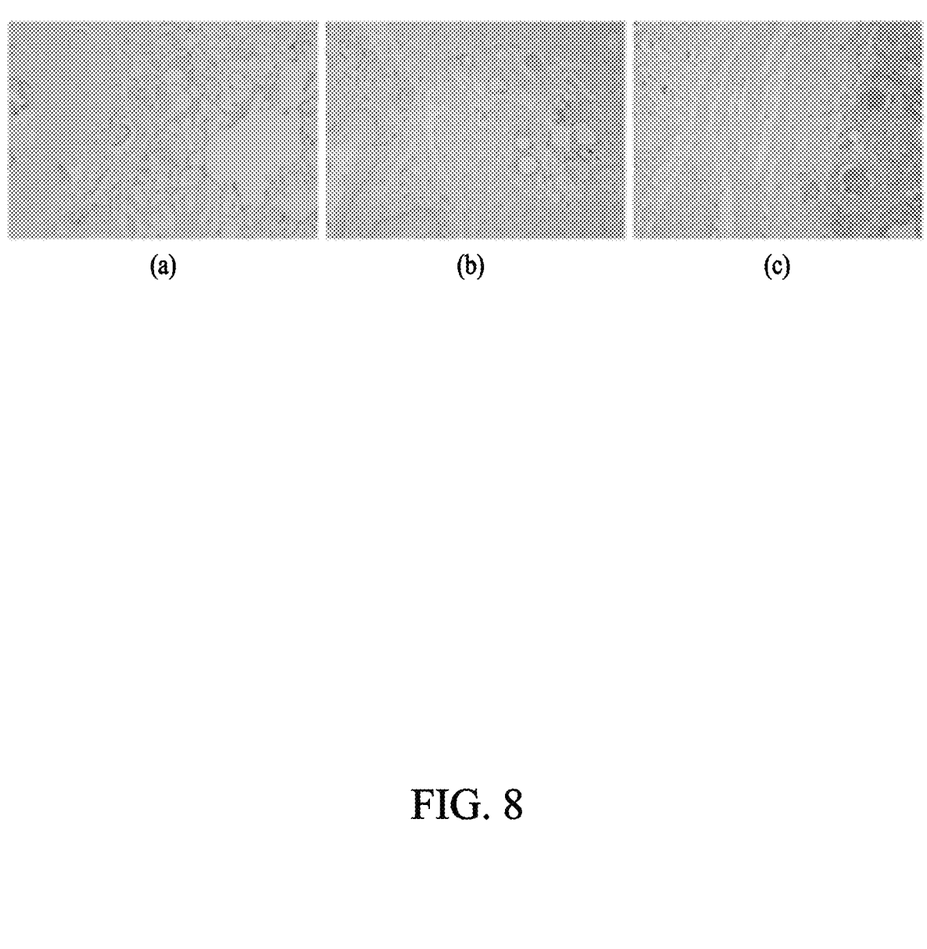
FIG. 8 is a view showing the results of each of 40-, 100-, and 100-fold magnification with an optical microscope after TNF-α staining of anal tissue 4 weeks after injecting an injection into three groups in Experimental Example 2 ((a) Example 1, (b) Comparative Example 1, and (c) Comparative Example 2).

FIG. 8 is a view showing the results of each of 40-, 100-, and 100-fold magnification with an optical microscope after TNF-α staining of anal tissue 4 weeks after injecting an injection into three groups in Experimental Example 3 ((a) Example 1, (b) Comparative Example 1, and (c) Dexol).

Referring to FIG. 8, it was identified that overall, the staining tended to be poor, but a strong staining reaction was shown in the experimental group injected in Comparative Example 2.

INDUSTRIAL APPLICABILITY

The in-vivo bulking agent of the present disclosure can exhibit a bulking effect when injected into the body and is highly biocompatible because a first composition in which silicone particles are coated with a zwitterionic polymer having a surfactant property is introduced into a second composition, whereby the bulking agent can inhibit inflammatory responses in vivo. Therefore, the agent can be usefully used in the field of treatment of diseases requiring bulking in the body after injection.

The invention claimed is:

1. An in-vivo bulking agent formulated as an injectable composition, comprising:
    a first composition including polydimethylsiloxane (PDMS) particles and a zwitterionic polymer surrounding a surface of the polydimethylsiloxane particles; and
    a second composition having a viscosity of 100 to 1500 cps at room temperature, wherein the zwitterionic polymer of the first composition has a surfactant property, and wherein the zwitterionic polymer is included in an amount of 0.1 to 5 parts by weight of based on 100 parts by weight of the polydimethylsiloxane particles and the zwitterionic polymer is a random copolymer including a first monomer having a zwitterion ion and a second monomer containing an acrylic acid ester, wherein the first monomer is one or more selected from the group consisting of methacryloyloxyethyl phosphorylcholine (MPC), carboxybetaine methacrylate (CBMA), and sulfobetaine methacrylate (SBMA).

2. The in-vivo bulking agent of claim 1, wherein the in-vivo bulking agent satisfies the following Equation 1:

$$|V2-V1| \times 1/100 \leq 0.1 \qquad \text{[Equation 1]}$$

wherein, V1 refers to a volume occupied by the in-vivo bulking agent when the in-vivo bulking agent is injected into a subject, and V2 refers to a volume occupied by the in-vivo bulking agent in the body 4 weeks after injection of the in-vivo bulking agent into the subject.

3. The in-vivo bulking agent of claim 1, wherein the first composition is in the form of particles having an average particle diameter in the range of 50 to 500 μm.

4. The in-vivo bulking agent of claim 1, wherein the second monomer is one or more selected from the group consisting of butyl methacrylate (BMA), 3-[tris(trimethylsiloxy)silyl]propyl methacrylate (TRIS) and dodecyl methacrylate (DMA).

5. The in-vivo bulking agent of claim 1, wherein the second composition is hyaluronic acid (HA) or collagen.

6. The in-vivo bulking agent of claim 1, wherein the second composition is added in an amount of 55 to 65% (v/v) based on the total in-vivo bulking agent.

7. The in-vivo bulking agent of claim 1, wherein the agent is used for prevention or treatment of sphincter-related diseases.

8. The in-vivo bulking agent of claim 7, wherein the sphincter-related disease is at least one disease selected from the group consisting of a urinary incontinence disease, fecal incontinence, gastroesophageal reflux, and vesicoureteral reflux.

9. The in-vivo bulking agent of claim 1, wherein the agent is used for a plastic surgery procedure.

10. An injection including the in-vivo bulking agent according to claim 1.

11. A method for preventing or treating a sphincter-related disease, the method comprising injecting the in-vivo bulking agent according to claim 1 into a subject.

12. The method of claim 11, wherein the sphincter-related disease is at least one disease selected from the group consisting of fecal incontinence, rectal incontinence, gastroesophageal reflux, a urinary incontinence disease, and vesicoureteral reflux.

13. A method for preparing an in-vivo bulking agent formulated as an injectable composition, the method comprising:

mixing polydimethylsiloxane particles and a zwitterionic polymer to prepare a first composition in which the zwitterionic polymer is surrounded on a surface of the polydimethylsiloxane particles; and dispersing the first composition in a second composition having a viscosity of 100 to 1500 cps at room temperature;

wherein the first composition includes 0.1 to 5 parts by weight of the zwitterionic polymer based on 100 parts by weight of the polydimethylsiloxane particles and the zwitterionic polymer is a random copolymer including a first monomer having a zwitterion ion and a second monomer containing an acrylic acid ester, wherein the first monomer is one or more selected from the group consisting of methacryloyloxyethyl phosphorylcholine (MPC), carboxybetaine methacrylate (CBMA), and sulfobetaine methacrylate (SBMA).

14. The method of claim 13, wherein the preparation of the first composition includes:

preparing a mixed solution by adding the polydimethylsiloxane particles and the zwitterionic polymer to a solvent;

dispersing the polydimethylsiloxane particles and the zwitterionic polymer in the solvent by ultrasonicating the mixed solution; and centrifuging the ultrasonicated mixed solution, and then obtaining powder to prepare the first composition in which the zwitterionic polymer is surrounded on the surface of the polydimethylsiloxane particles.

* * * * *